United States Patent [19]
Thibodeau et al.

[11] Patent Number: 5,578,450
[45] Date of Patent: Nov. 26, 1996

[54] TUMOR-SPECIFIC GENOMIC INSTABILITY AS A PROGNOSTIC INDICATOR

[75] Inventors: Steven N. Thibodeau, Rochester; Gary D. Bren, Chatfield, both of Minn.

[73] Assignee: Mayo Foundation for Medical Education and Research, Rochester, Minn.

[21] Appl. No.: 455,637

[22] Filed: May 31, 1995

Related U.S. Application Data

[63] Continuation of Ser. No. 21,960, Feb. 24, 1993, abandoned.
[51] Int. Cl.$^6$ ............................ C12Q 1/68; C12P 19/34
[52] U.S. Cl. .................. 435/6; 435/91.2; 935/77; 935/78
[58] Field of Search .................. 435/6, 91.2; 935/72, 935/78

[56] References Cited

U.S. PATENT DOCUMENTS

5,075,217 12/1991 Weber ........................................ 435/6

OTHER PUBLICATIONS

Perucho et al., *Cell* 27:467–476 (1981).
Bernues et al., *Gene* 108:269–274 (1991).
Dracopoli et al., Mapping the Human Amylase Gene Cluster on the Proximal Short Arm of Chromosome 1 Using a Highly Informative (CA)n Repeat, *Genomics* 7:97–102 (1990).
Nurnberg et al., DNA Fingerprinting With the Oligonucleotide Probe (CAC)5/(GTG)5: Somatic Stability and Germline Mutations, *Hum. Genet.* 84:75–78 (1989).
Tautz, Hpervariability of Simple Sequences as a General Source for Polymorphic DNA Markers, *Nucleic Acids Res.* 17:6463–71 (1989).
Weissenbach et al., A Second–Generation Linkage Map of the Human Genome, *Nature* 359:794–801 (1992).
Jeffreys et al., Individual–Specific Fingerprints of Human DNA, *Nature* 316:76–79 (1985).
Jeffreys et al., Minisatellite Repeat Coding as a Digital Approach to DNA Typing, *Nature* 354:204–209 (1991).
Lagoda et al., Increased Detectability of Somatic Changes in DNA from Human Tumours After Probing with "Synthetic" and Genome–Derived Hypervariable Multilocus Probes, *Hum Genet.*, 84:35–40.
Kremer et al., Mapping of DNA Instability at the Fragile X to a Trinucleotide Repeat Sequence p(CCG)n, *Science* 252:1711–14 (1991).
Fu et al., Variation of the CGG Repeat at the Fragile X Site Results in Genetic Instability: Resolution of the Sherman Paradox, *Cell* 67:1047–58 (1991).

Hirst et al., Genotype Prediction in the Fragile X Syndrome. *J. Med. Genet.* 28:824–29 (1991).
La Spada et al., Androgen Receptor Gene Mutations in X–Linked Spinal and Bulbar Muscular Atrophy *Nature* 352:77–79 (1991).
Mahadevan et al., Myotonic Dystrophy Mutation: An Unstable CTG Repeat in the 3' Untraslated Region of the Gene, *Science* 255: 1253–55 (1992.
Brook et al., Molecular Basts of Myotonic Dystrophy: Extension of a Trinucleotide (CTG) Repeat at the 3' end of a Transcript Encoding a Protein Kinase Family Member, *Cell* 68:799–808 (1992).
Vogelstein et al., Genetic Alterations During Colorectal–Tumor Development, *N. Engl. J. Med.* 319:525–32 (1988).
Kern et al., Allelic Loss in Colorectal Carcinoma, *J. Am. Med. Assoc.* 261:3099–3103 (1989).
Offerhaus et al., The Relationship of DNA Aneuploidy to Molecular Genetic Alterations in Colorectal Carcinoma, *Gastroenterology* 102:1612–19 (1992).
Bufill et al., Colorectal Cancer: Evidence for Distinct Genetic Categories Based on Proximal or Distal Tumor Location, *Ann. Int. Med.* 113:779–88 (1990).
Ghahremani et al., Colorectal Carcinomas:Diagnostics Implications of their Changing Frequency and Anatomic Distribution, *World J. Surg.* 13:321–25 (1989).
DeLattre et al., Multiple Genetic Alterations in Distal and Proximal Colorectal Cancer, *Lancet* 2:353–56 (1989).
Rogers et al., Analysis of DNA in Fresh and Fixed Tissue by the Polymerase Chain Reaction, *Am. J. Pottiol.* 136:541–48 (1990).
J. L: Weber and P. E. May, Abundant Class of Human DNA Polymorphisms Which Can Be Typed Using the Polymerase Chain Reaction, *Am. J. Hum. Genet.* 44:388–96 (1989).
Y. Matsumura and D. Tarin, DNA Fingerprinting Survey of Various Human Tumors and Their Metastases, *Cancer Res.* 52:2174–2179 (1992).
M. F. Fey et al., Assessment of Clonality in Gastrointestinal Cancer by DNA Fingerprinting, *J. Clin. Invest.* 82:1532–37 (1988).
J. L. Weber, Informativeness of Human (dC–dA)n(dG–dT)n Polymorphisms, *Genomics* 7:524–30 (1990).

*Primary Examiner*—Stephanie W. Zitomer
*Attorney, Agent, or Firm*—Fish & Richardson P.C., P.A.

[57] ABSTRACT

A method for assessing the level of genomic instability in a malignant tumor is described. The method involves comparison of the structure of one or more interspersed repetitive sequence loci in tumor and corresponding normal tissue samples. Microsatellite repetitive sequences are one useful form of interspersed repetitive sequence that may be employed to characterize the genomic instability associated with some malignant tumors. This assessment provides an additional prognostic indicator for patients having such malignant tumors.

14 Claims, 3 Drawing Sheets

Fig. 4
Mfd 27

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear     ( v i i i ) POSITION IN GENOME:
        ( A ) CHROMOSOME/SEGMENT: 5q11.2- q13.3
        ( B ) MAP POSITION: D5S107

( x i ) SEQUENCE DESCRIPTION: SEQ ID NO:1:

GATCCACTTT AACCCAAATA C            21

( 2 ) INFORMATION FOR SEQ ID NO:2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear     ( v i i i ) POSITION IN GENOME:
        ( A ) CHROMOSOME/SEGMENT: 5q11.2- q13.3
        ( B ) MAP POSITION: D5S107

( x i ) SEQUENCE DESCRIPTION: SEQ ID NO:2:

GGCATCAACT TGAACAGCAT            20

( 2 ) INFORMATION FOR SEQ ID NO:3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear     ( v i i i ) POSITION IN GENOME:
        ( A ) CHROMOSOME/SEGMENT: 17p12- p11.1
        ( B ) MAP POSITION: D17S261

( x i ) SEQUENCE DESCRIPTION: SEQ ID NO:3:

CAGGTTCTGT CATAGGACTA                                                                                           20

( 2 ) INFORMATION FOR SEQ ID NO:4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear     ( v i i i ) POSITION IN GENOME:
        ( A ) CHROMOSOME/SEGMENT: 17p12- p11.1
        ( B ) MAP POSITION: D17S261

( x i ) SEQUENCE DESCRIPTION: SEQ ID NO:4:

TTCTGGAAAC CTACTCCTGA                                                                                           20

( 2 ) INFORMATION FOR SEQ ID NO:5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear     ( v i i i ) POSITION IN GENOME:
        ( A ) CHROMOSOME/SEGMENT: 18q
        ( B ) MAP POSITION: D18S34

( x i ) SEQUENCE DESCRIPTION: SEQ ID NO:5:

CAGAAAATTC TCTCTGGCTA                                                                                           20

( 2 ) INFORMATION FOR SEQ ID NO:6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear     ( v i i i ) POSITION IN GENOME:
        ( A ) CHROMOSOME/SEGMENT: 18q
        ( B ) MAP POSITION: D18S34

( x i ) SEQUENCE DESCRIPTION: SEQ ID NO:6:

CTCATGTTCC TGGCAAGAAT                                                                                           20

( 2 ) INFORMATION FOR SEQ ID NO:7:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear     ( v i i i ) POSITION IN GENOME:
        ( A ) CHROMOSOME/SEGMENT: 15q11- qter     ( x i ) SEQUENCE DESCRIPTION: SEQ ID NO:7:

TTGACCTGAA TGCACTGTCA                                                                                           20

( 2 ) INFORMATION FOR SEQ ID NO:8:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear (viii) POSITION IN GENOME:
    (A) CHROMOSOME/SEGMENT: 15q11- qter (xi) SEQUENCE DESCRIPTION: SEQ ID NO:8:

TTCCATACCT GGCAACGAGT    20

(2) INFORMATION FOR SEQ ID NO:9:

(i) SEQUENCE CHARACTERISTICS:
        (A) LENGTH: 20
        (B) TYPE: nucleic acid
        (C) STRANDEDNESS: single
        (D) TOPOLOGY: linear (x) PUBLICATION INFORMATION:
        (A) AUTHORS: Peterson, M.G.
            Tanese, N.
            Pugh, B.F.
            Tjian, R.
        (B) TITLE: Functional domains and upstream activation
            properties of cloned human TATA binding protein
        (C) JOURNAL: Science
        (D) VOLUME: 248
        (F) PAGES: 1625-1630
        (G) DATE: 1990
        (K) RELEVANT RESIDUES IN SEQ ID NO: 352 - 371

(xi) SEQUENCE DESCRIPTION: SEQ ID NO:9:

ACTGACCCCA CAGCCTATTC    20

(2) INFORMATION FOR SEQ ID NO:10:

(i) SEQUENCE CHARACTERISTICS:
        (A) LENGTH: 20
        (B) TYPE: nucleic acid
        (C) STRANDEDNESS: single
        (D) TOPOLOGY: linear (x) PUBLICATION INFORMATION:
        (A) AUTHORS: Peterson, M.G.
            Tanese, N.
            Pugh, B.F.
            Tjian, R.
        (B) TITLE: Functional domains and upstream activation
            properties of cloned human TATA binding protein
        (C) JOURNAL: Science
        (D) VOLUME: 248
        (F) PAGES: 1625-1630
        (G) DATE: 1990
        (K) RELEVANT RESIDUES IN SEQ ID NO: 618 - 637

(xi) SEQUENCE DESCRIPTION: SEQ ID NO:10:

CAAGGGTGCA GTTGTGAGAG    20

TUMOR-SPECIFIC GENOMIC INSTABILITY AS A PROGNOSTIC INDICATOR

This invention was made with government support under Grant No. CA 15083-18E8.1 awarded by the National Institutes of Health. The government has certain rights in the invention.

This is a continuation of application Ser. No. 08/021,960, filed Feb. 24, 1993, now abandoned.

FIELD OF THE INVENTION

This invention relates generally to development of clinical prognoses for cancer patients by analysis of tumor nucleic acids for evidence of genomic instability. More specifically, this invention relates to a method for comparing the structural integrity of interspersed reptitive sequences in tumor and corresponding normal tissue as a prognostic indicator.

BACKGROUND OF THE INVENTION

In recent years there has been significant progress in deciphering the molecular changes accompanying malignant transformation. A large number of tumors have been characterized as carrying a variety of chromosomal and submicroscopic genomic modifications, including activation of dominant-acting proto-oncogenes, inactivation of tumor suppressor genes and inactivation of metastasis suppressor genes. It is presumed that such tumors are descended from cell lineages that have accumulated a set of critical genetic lesions through random and relatively rare mutations at defined chromosomal locations. As an alternative tumor mechanism, some have postulated that a generalized, disseminated genomic instability, with attendant increased frequency of mutations at numerous unrelated loci, may represent a primary genetic mechanism in some tumors.

In a normal cell, multiple metabolic pathways control the overall accuracy of various functions, including DNA replication and repair, cell division and differentiation. A generalized genomic instability potentially could arise from disruption of one or more of these functions, including DNA replication, post-replicative proofreading, DNA repair, cell cycle checkpoint proteins, and DNA recombination. Mutations in genes that cause a generalized increase in the frequency of substitutions, insertions, deletions or other structural changes throughout the genome can be classified as "mutator" mutations.

Several clinical correlates have been cited in support of the theory that mutations in "mutator genes" may alter the regulation of a wide spectrum of genes, including those genes responsible for tumorigenesis. For example, individuals with the inherited disorder xeroderma pigmentosum are defective in excision repair of DNA. A clinical correlate of this condition is a predisposition of these individuals to skin cancer following exposure to ultraviolet light.

In summary, malignant transformation may involve either of the following genetic pathways:

(1) accumulation in selected cell lineages of random but relatively infrequent mutations in proto-oncogenes, tumor suppressor genes and other genes directly related to tumorigenesis.

(2) mutation(s) in a mutator gene with resultant genomic instability.

There may be functional overlap in these two mechanisms in the sense that mechanism (2) may lead secondarily to mutations in known proto-oncogenes and tumor suppressor genes. However, the generalized and disseminated genomic instability of mechanism (2) may influence carcinogenesis through a wide array of known and unknown genetic mechanisms. As such, there may be little or no correlation between elevated levels of genomic instability and known mutational changes in characterized tumor-related genes. Moreover, it is conceivable that patients having tumors deriving from mechanism (2) may enjoy a relatively favorable prognosis compared to patients having tumors deriving from mechanism (1). This is due to the tendency of tumor cells having a generalized and disseminated genomic instability to continue to accumulate mutational changes, leading to cell dysfunction and/or death. That is, these tumors may be relatively self-limiting in comparison to tumors deriving from mechanism (1).

While a variety of nucleic add probe-based assays are available to detect structural alterations in known tumor-related genes, there has been no reliable indicator of mechanisms involving generalized genomic instability in tumor formation. Nor has there been a reliable test to distinguish tumors arising from random mutations in tumor-related genes from those tumors arising from a more generalized genomic instability. The present inventors have discovered that monitoring the structural integrity, or sequence organization, of one or more members of selected interspersed repetitive sequence families provides a method for assessing genomic instability in tumors and for correlating such instability with tumor location and clinical prognosis.

One form of interspersed repetitive sequence in humans is the "microsatellite" class of sequences. MicroSatellite sequences of the form $(CA)_n \cdot (GT)_n$ constitute one of the most abundant classes of repetitive DNA families in human DNA. Approximately 50,000–100,000 $(CA)_n$-repeats are scattered throughout the human genome. Many, if not most, of these $(CA)_n$-repeats exhibit length polymorphisms. Dracopoli et al., Mapping the Human Amylase Gene Cluster on the Proximal Short Arm of Chromosome 1 Using a Highly Informative $(CA)_n$ Repeat, *Genomics* 7:97–102 (1990); Nurnberg et al., DNA Fingerprinting With the Oligonucleotide Probe $(CAC)_5/(GTG)_5$: Somatic Stability and Germline Mutations, *Hum. Genet.* 84:75–78 (1989); Tautz, Hypervariability of Simple Sequences as a General Source for Polymorphic DNA Markers, *Nucleic Acids Res.* 17:6463–71 (1989). Although the rate of new mutations at these sites is slightly increased compared to other genomic sites, the overall rate is still quite low. In general, alleles at these sites are stably inherited from one generation to another. In fact, these markers have now been identified as one of the most useful classes of DNA polymorphism for the purpose of linkage analysis. Weissenbach et al., A Second-Generation Linkage Map of the Human Genome, *Nature* 359:794–801 (1992).

Although specific forms of genomic instability previously have not been correlated with specific tumors or with tumor locations and tumor prognoses, probes directed toward "minisatellite" interspersed repetitive sequence families have detected novel fragments in various malignancies. In comparison to microsatellites, minisatellites are characterized by more complex short repetitive stretches of noncoding sequences. Moreover, minisatellite loci tend to be clustered on the tips of chromosome arms. Weissenbach et al., at 794.

Southern blot analysis of genomic DNA with probes consisting of minisatellite sequences reveals an array of fragments that wiry in molecular weight. Each fragment represents multiple non-contiguous loci within the human genome. As such, these probes have been useful for multilocus fingerprinting of DNA. Jeffreys et al., Individual-Specific Fingerprints of Human DNA, *Nature* 316:76 (1985); Jeffreys et al., Minisatellite Repeat Coding as a Digital Approach to DNA Typing, *Nature* 354:204 (1991). In a similar fashion, alterations in multilocus microsatellite sequences of the form $(CA)_n$ may be detected in genomic Southern blots using probes comprising various $(CA)_n$ nucleotide stretches. However, a more rigorous investigation of mutational changes in individual microsatellite loci may be obtained by amplification of individual microsatellites using primer pairs directed to unique sequence flanking such microsatellites.

Additional bands or deleted bands have been observed in genomic blots of tumor DNA probed with $(CAC)_5$ and $(GTG)_5$ oligonucleotide probes. Lagoda et al., Increased Detectability of Somatic Changes in DNA from Human Tumours After Probing with "Synthetic" and "Genome-Derived" Hypervariable Multilocus Probes, *Hum. Genet.* 84:35–40 (1989). However, such changes were not correlated with genomic instability as related to particular tumor types, with particular anatomical groupings of tumors, or with clinical prognosis.

The sequences detected by minisatellite and microsatellite probes are not known to have any specific function. Thus, the abnormalities detected are not expected, in themselves, to be causally involved in tumor initiation or progression. However, heritable, unstable DNA elements recently have been identified as the basis of disease for three separate inherited disorders: (1) Fragile X syndrome, Kremer et al., Mapping of DNA Instability at the Fragile X to a Trinucleotide Repeat Sequence $p(CCG)_n$, *Science* 252:1711–14 (1991); Fu et al., Variation of the CGG Repeat at the Fragile X Site Results in Genetic Instability: Resolution of the Sherman Paradox, *Cell* 67:1047–58 (1991); Hirst et al., Genotype Prediction in the Fragile X Syndrome. *J. Med. Genet.* 28:824–29 (1991); (2) Kennedy's disease, La Spada et al., Androgen Receptor Gene Mutations in X-Linked Spinal and Bulbar Muscular Atrophy, Nature 352:77–79 (1991); and (3) Myotonic Dystrophy, Mahadevan et al., Myotonic Dystrophy Mutation: An Unstable CTG Repeat in the 3' Untranslated Region of the Gene, *Science* 255:1253–55 (1992); Brook et al., Molecular Basis of Myotonic Dystrophy: Extension of a Trinucleotide (CTG) Repeat at the 3' End of a Transcript Encoding a Protein Kinase Family Member, *Cell* 68:799–808 (1992). All available evidence suggests that amplification of a tri-nucleotide repeat is involved in the molecular pathology in each of these disorders. Although these trinucleotide repeats appear to be in non-coding DNA, they clearly are involved with perturbations of genomic regions that ultimately affect gene expression. Perturbations of various di- and tri-nucleotide repeats resulting from somatic mutation in tumor cells could also affect gene expression and/or gene regulation.

To investigate the role of disseminated genomic instability as a mechanism in tumorigenesis, it is useful to examine model systems in which tumors of potentially distinctive genetic backgrounds may be identified. Preliminary studies have indicated that different genetic mechanisms of tumorigenesis may be operative in different anatomical regions of the colorectal tract. On the one hand, evidence indicates that the process of tumorigenesis in at least some colorectal cancers proceeds through a series of genetic alterations in defined loci including both dominant and recessive acting proto-oncogenes. On the other hand, some colorectal cancers do not display such defined structural changes in known tumor-associated genes. Colorectal cancer therefore represents a useful model for analysis of disseminated genomic instability as a potential mechanism in cancer.

With respect to dominant acting proto-oncogenes in colorectal cancer, both carcinomas and the larger villous type of adenomas have shown point mutation in the ras proto-oncogene in roughly 50% of the cases. Vogelstein et al., Genetic Alterations During Colorectal-Tumor Development, *N. Engl. J. Med.* 319:525–32 (1988). C-myc mRNA has been found to be expressed at significantly higher levels in tumors compared to normal mucosa. Sikora et al., C-myc Oncogene Expression in Colorectal Cancer, *Cancer* 59:1289–95 (1987); Erisman et al., The C-myc Protein is Constitutively Expressed at Elevated Levels in Colorectal Carcinoma Cell Lines, *Oncogene* 2:367–78 (1988).

With respect to recessive acting proto-oncogenes (e.g., tumor-suppressor genes), several studies have demonstrated allelic loss in colorectal carcinoma. Loss of allelic heterozygosity (LOH) on a particular chromosome in cells of a tumor provides indirect evidence for the presence of a tumor suppressor gene(s) on that portion of the chromosome involved in the LOH. It has been proposed that tumor suppressor gene function can be lost through mutational inactivation of one member of an allelic pair and an accompanying chromosomal deletion that leads to physical loss or inactivation of the other member of the allelic pair. The chromosomal deletion is detected as an LOH using a polymorphic marker present in the same chromosomal region as the tumor suppressor gene. The most frequent sites of allelic loss in colon cancer appear to be on chromosomes 17 and 18 (each exhibiting LOH in nearly 75% of colorectal carcinomas); another one-third to one-half of such tumors exhibit LOH on chromosome 5. Candidate tumor suppressor genes are MCC and APC (familial adenomatous polyposis locus) on chromosome 5q, p53 on chromosome 17p and DCC (deleted in colorectal carcinoma) on chromosome 18q. Kinzler et al., Identification of a Gene Located at Chromosome 5q21 That Is Mutated in Colorectal Cancer, *Science* 251:1366–70 (1991); Kinzler et al., Identification of FAP Locus Genes from Chromosome 5q21, *Science* 253:661–64 (1991); Baker et al., Chromosome 17 Deletions and p53 Gene Mutations in Colorectal Carcinomas, *Science* 244:217–21 (1989), Fearon et al., Identification of a Chromosome 18q Gene That Is Altered in Colorectal Cancers, *Science* 247:49–56 (1990). In addition to chromosomes 5, 17 and 18, other chromosomes including chromosomes 1, 6, 8, 14 and 22 have been implicated in the genesis of colorectal cancer.

To date, results of LOH studies in colorectal cancer have shown a significant correlation with the site of the tumor. Delattre et al., Multiple Genetic Alterations in Distal and Proximal Colorectal Cancer, *The Lancet* 2:353–56 (1989); Kern et al., Allelic Loss in Colorectal Carcinoma, *J. Am. Med. Assoc.* 261:3099–3103 (1989); Offerhaus et al., The Relationship of DNA Aneuploidy to Molecular Genetic Alterations in Colorectal Carcinoma, *Gastroenterology* 102:1612–19 (1992). Specifically, it appears that allelic loss on chromosomes 5, 17 and 18 occurs more frequently in distal tumors than in proximal tumors. Such differences suggest that proximal and distal tumors may arise through different pathogenetic mechanisms, and that at least two genetic categories of colorectal cancer may exist. In fact, a growing body of evidence suggests that tumors of the proximal colon differ from tumors of the distal colon. Bufill et al., Colorectal Cancer: Evidence for Distinct Genetic Categories Based on Proximal or Distal Tumor Location, *Ann. Int. Med.* 113:779–88 (1990). This evidence, which stems from developmental and biological differences within the normal colon and various characteristics noted in colorectal cancer, includes the following:

A. Developmental.

The area extending from the cecum to the proximal two-thirds of the transverse colon is derived from the embryonic mid gut while the distal third of the transverse colon to the rectum is derived from the embryonic hind gut. Langman, J., *Medical Embryology*, 4th Ed. (1981). The distinct embryologic origin of these two regions is also reflected in different vascular supplies. Subsequent development leads to a number of properties that differ between the proximal and distal colon, such as the distribution of hormone producing cells.

B. Biological.

Biological differences between proximal and distal colon include differences in ability to metabolize various carcinogens, differences in the expression of cell surface antigens, and differences in enzymatic activities. Stralka et al., Cytochrome P-450 Activity and Distribution in the Human Colon Mucosa, *Cancer* 64:2111–16 (1980); Hughes et al., Antigen Expression in Normal and Neoplastic Colonic Mucosa: 3 Tissue-Specific Antigens Using Monoclonal Antibodies to Isolated Colonic Glands, *Cancer Res.* 46:2164–71 (1986); Tari et al., The Relation Between Ornithine Decarboxylase Activity and the Location of Colorectal Cancers, *Gastroenterology* 98:A313 (1990).

C. Epidemiological.

The relative incidence of proximal and distal tumors appears to vary in relation to the total incidence in a given region. In regions with a low incidence, proximal tumors predominate. In high risk areas, distal tumors predominate. Furthermore, the incidence of proximal tumors in the population at large appears to be increasing. Ghahremani et al., Colorectal Carcinomas: Diagnostics Implications of their Changing Frequency and Anatomic Distribution, *World J. Surg.* 13:321–25 (1989); Fleshner et al., Age and Sex Distribution of Patients with Colorectal Cancer, *Dis. Rectum.* 32:107–11 (1989).

D. Inheritance.

Colon cancer that appears in patients with familial adenomatous polyposis tends to be left-sided while those that occur in hereditary non-polyposis rectal cancer tend to be right-sided. Lynch et al., Hereditary Non-Polyposis Rectal Cancer (Lynch Syndromes I and II). II. Biomarker Studies, *Cancer* 56:939–51 (1985).

E. Other Proto-oncogenes.

Several studies have shown that tumors expressing deregulated c-myc are formed more frequently in the distal colon. Rothberg et al., Evidence that C-myc Expression Defines Two Genetically Distinct Forms of Colorectal Adenocarcinoma, *Br. J. Cancer* 52:629–32 (1985); Sikora et al., C-myc Oncogene Expression in Colorectal Cancer, *Cancer* 59:1289–95 (1987); Erisman et al., The C-myc Protein is Constitutively Expressed at Elevated Levels in Colorectal Carcinoma Cell Lines, *Oncogene* 2:367–78 (1988). On the other hand, mutations in the ras proto-oncogene occur moire frequently in proximal tumors. Offerhaus et al., The Relationship of DNA Aneuploidy to Molecular Genetic Alternations in Colorectal Carcinoma, *Gastroenterology* 102:1612–19 (1992).

F. Tumor DNA Content.

Analysis of DNA content by flow cytometry has shown that aneuploidy is more frequently encountered in distal tumors than in proximal tumors. Delattre et al., Multiple Genetic Alternations in Distal and Proximal Colorectal Cancer, *Lancet* 2:353–56 (1989).

All of the above-referenced differences suggest the tendency of distinct pathogenetic mechanisms to be responsible for cancers of the proximal and distal colon. Although tumor suppressor genes appear to play a more prominent role in the development of tumors in the distal as opposed to the proximal colon, the underlying genetic lesions in proximal tumors have been poorly understood. Nevertheless, knowledge of the molecular genetic mechanisms involved in cancer will have an enormous impact on clinical practice and on the design of future prospective research studies covering new methods of surgical adjuvant therapy. There is an ongoing need for new prognostic indicators to more precisely identify those patients that may benefit from adjuvant therapy and those patients at high risk for tumor recurrence.

SUMMARY OF THE INVENTION

The present inventors have discovered a method for detecting genomic instability in malignant tumors through analysis of interspersed repetitive sequences in the DNA of such tumors. The analysis can provide a prognostic indicator for patients having such tumors. The method involves obtaining genomic DNA from a tumor and from normal tissue of the same patient and evaluating one or more interspersed repetitive sequence loci in the respective DNAs. The structural status, or sequence organization, of the interspersed repetitive sequences in the tumor is compared with the structural status of the interspersed repetitive sequences in the corresponding normal tissue. The results of this analysis may be correlated with the presence or absence of genomic instability in the tumor genome and with the clinical prognosis of the patient having the tumor.

The interspersed repetitive sequences examined may be minisatellite or microsatellite sequences. For example, various di- or tri-nucleotide microsatellite repeats may be examined at one or more loci. In particular, a microsatellite dinucleotide repeat of the form $(CA)_n \cdot (GT)_n$ has been found useful for analysis of colorectal tumors. In one embodiment, selected di- and tri-nucleotide repeat loci are examined using sequence amplification procedures. Appropriate primers for polymerase-based amplification of selected loci are chosen and used to amplify, for example, one or more selected $(CA)_n$ repeat loci. Polymerase chain reaction or other amplification methods may be used in the analysis. Primer pairs may be selected to hybridize to unique sequence flanking the 3' and 5' ends of the $(CA)_n$ repeat region of the locus. The apparent fragment sizes of the amplified DNA's are compared in order to evaluate whether or not the $(CA)_n$ repeat region has undergone a structural alteration (e.g., insertion/amplification, deletion) in the tumor DNA that is not seen in the corresponding normal DNA.

The presence of structural alterations in one or more interspersed repetitive sequence loci in a tumor is interpreted as evidence for a generalized, disseminated genomic instability. The structural alterations can be correlated with the clinical prognosis of the patient having the tumor.

BRIEF DESCRIPTION OF THE FIGURES

FIG. 1 depicts autoradiographs of amplified fragments obtained with primer pairs specific for (CAn) di-nucleotide repeat microsatellite loci. Shown is an analysis of amplified fragments by denaturing gel electrophoresis for two $(CA)_2$-repeats: Mfd 27 (Panel A) and Mfd 41 (Panel B). Panel A, lanes 1 and 2, 8 and 9, and 10 and 11 are from paired normal (1st) and tumor (2nd) tissue. Lanes 4, 5 and 7 are results from three synchronous tumors with lane 3 representing the normal tissue from that patient. Panel B shows a comparison of normal tissue to that of tumor tissue derived from fresh frozen and paraffin embedded material. N, normal tissue; T, tumor tissue; TF, tumor from fresh frozen material; TP, tumor from paraffin embedded material.

DETAILED DESCRIPTION OF THE INVENTION

The present inventors have discovered a type of genetic alteration appearing in malignant tumor cell DNA and not in normal cell DNA. These alterations are interpreted to be indicative of a disseminated, generalized form of genomic instability associated with at least one mechanism of tumorigenesis. This form of genomic instability may be detected through examination of interspersed repetitive DNA sequences. Preferably these sequences are members of the "minisatellite" and "microsatellite" interspersed repetitive sequence families. Most preferably these sequences are members of the microsatellite interspersed repetitive sequence families.

In order to characterize alterations at these sites in detail, DNA from colorectal cancers or other tumors may be examined using gene amplification-based assays for individual loci comprising the $(CA)_n$ form of microsatellite interspersed repetitive sequence. Loci selected for such analysis may be selected for proximity to known dominant acting proto-oncogenes, tumor suppressor genes or chromosome locations otherwise suspected of being involved in genetic changes accompanying malignant transformation. Alternatively, other loci may be chosen at relatively random locations on various chromosomes. Tumor-specific changes in the apparent fragment sizes of such alleles can vary from single 2 base-pair (bp) alterations to larger insertions/amplifications or deletion events. For purposes of data analysis of genomic instability, the present inventors have classified the larger insertion/amplification/deletion events as "Type I" mutations and the smaller (e.g. 2 bp) alterations as "Type II" mutations. Other classifications of DNA structural changes in various tumor systems may be appropriate depending on the array of mutational changes in interspersed repetitive sequences observed in such tumors.

For examination of generalized genomic instability in tumors, tumor samples may be removed from patients diagnosed with malignant tumors. Tumor tissue may be obtained through biopsies or following surgical removal of all or part of the tumor. DNA from normal tissue of such patients may be obtained from peripheral white blood cells, from normal tissue infiltrates of the tumors, from biopsy or surgical removal of normal tissue adjacent to the tumors or by other methods known to those skilled in the art. DNA may be obtained from unfixed or frozen tissue or, alternatively, from tissue prepared for histology. For example, DNA may be obtained from tumor tissue embedded in paraffin.

In a preferred embodiment, tumor and tissue samples are processed to ensure that the tumor samples contain an operable fraction of tumor cells and that the normal tissue samples are operably free of tumor cells. In the experiments reported in the Examples below, the tumor samples were processed to have at least 70% tumor cells. The primary consideration in processing of tumor tissue is that a sufficient, or operable, fraction of tumor tissue is present to allow detection of DNA structural changes in tumor DNA samples compared to normal tissue DNA samples. Although 70% tumor cells was chosen as the minimum fraction of tumor cells in the experiments reported in the Examples, below, other percentages may be appropriate as long as nucleic acid sequence changes are correctly interpretable. The normal tissue sample should be operably free of tumor cells, such that any contaminating tumor cells do not cause a misreading of the normal band positions. Preferably the normal tissue sample is absolutely free of tumor cells. Operable fractions of cells for a given tumor system may be readily determined through routine preliminary experiments. For example, relatively pure samples of normal and tumor cells may be mixed in various proportions and the resulting mixtures used to provide DNA samples. Results from the mixed samples are then readily evaluated for accuracy of results compared to the pure samples.

DNA may be isolated from fresh or frozen tissue using standard methods as described in, for example, Sambrook et al., *Molecular Cloning: A Laboratory Manual*, 2d Ed. (1989), pages 9.16–9.23. Isolation of DNA from paraffin-embedded tissues is described, for example, by Jackson et al., Tissue Extraction of DNA and RNA and an Analysis by the Polymerase Chain Reaction, *J. Clin. Pathol.* 43:499–504 (1990) and Rogers et al., Analysis of DNA in Fresh and Fixed Tissue by the Polymerase Chain Reaction, *Am. J. Pathol.* 136:54148 (1990).

Once the genomic DNA is isolated from the tumors and normal tissues, polymerase chain reactions or other gene amplification reactions may be carried out using standard methods. Analysis of microsatellite sequences by polymerase chain reaction, for example, may follow the methods of Weber and May, Abundant Class of Human DNA Polymorphisms Which Can Be Typed Using the Polymerase Chain Reaction, *Am. I. Hum. Genet.* 44:388–96 (1989). Primer pairs are selected to hybridize to the DNA flanking the interspersed repetitive sequence loci at selected chromosomal locations. Microsatellite alleles may be chosen, for example, for their proximity to regions of chromosomes that have been implicated in allelic loss in various tumors. Conversely, other alleles may be selected specifically for chromosomal locations known to have a low frequency of allelic loss in colorectal or other cancers.

Aliquots of the amplified DNA's may be mixed with formamide sample buffer and electrophoresed on standard denaturing polyacrylamide DNA sequencing gels. Aliquots of the tumor and tissue DNA from the same patient and amplified using the same primer pair are loaded next to one another in the gel. Gels are then fixed, dried and processed for autoradiography. The lanes containing amplified tumor and tissue DNA are compared to one another to determine the mutational status of the amplified tumor DNA at the locus tested.

A variety of gene amplification techniques may be used for analysis of individual loci of interspersed repetitive sequences. Such methods may include, without limitation, Polymerase Chain Reaction (PCR), Saiki et al., Enzymatic Amplification of Beta-Globin Genomic Sequences and Restriction Site Analysis for the Diagnosis of Sickle Cell Anemia, *Science* 230:1350–54 (1985); Ligase Chain Reaction (LCR), Wu and Wallace, The Ligation Amplification Reaction (LAR)-Amplification of Specific DNA Sequences Using Sequential Rounds of Template-Dependent Ligation, *Genomics* 4:560–69 (1989) and Landegren et al., A Ligase Mediated Gene Detection Technique, *Science* 241:1077–80 (1988); Q-beta-Replicase Template Amplification (Q-beta), Lomeli et al., Quantitative Assays Based on the Use of Replicatable Hybridization Probes, *Clin. Chem.* 35:1826–31 (1989); and Strand Displacement Activation (SDA), Walder et al., Isothermal in vitro Amplification of DNA by a Restriction Enzyme/DNA Polymerase System, *Proc. Nat'l Acad. Sci. USA* 89:392–96 (1992). RNA-based amplification methods may be used for those interspersed repetitive sequences that are expressed as RNA. An example of an RNA-based amplification method is Self-Sustained Sequence Replication (3SR), Guatelli et al., Isothermal In Vitro Amplification of Nucleic Acids by a Multi-enzyme Reaction Modified After Retroviral Replication, *Proc. Nat'l Acad. Sci. USA* 87:1874 (1990).

As an alternative to analysis of interspersed repetitive sequence loci using sequence amplification methods, genomic instability also may be examined through analysis of the total population of selected microsatellite and/or minisatellite DNA families. For example, sequences comprising $(CA)_n$ oligonucleotides may be used as probes of genomic southern blots to assess the overall structural integrity of the $(CA)_n$ interspersed repetitive sequence family. Such "whole-family" scanning, although less discriminating of individual loci than the amplification-based analysis described above, may be useful for particular tumor systems.

The present inventors have discovered that structural alterations of interspersed repetitive sequences, as sign posts of generalized genomic instability, may be correlated with identifiable tumor sub-groupings and clinical prognosis. For example, differences in genomic instability as revealed by alterations in interspersed repetitive sequences have been found by the present inventors to vary with anatomical location of tumors within the colorectal region and with disease recurrence and survival. As discussed above, such sublocations or subgroupings of primary tumors may tend to arise by distinct genetic mechanisms.

Similar phenomena also may be expected to occur in other organ systems. For example, although not providing correlations with anatomical subgroupings of primary tumors or with clinical prognosis, several studies have demonstrated alterations in interspersed repetitive sequences in diverse tumor systems including stomach carcinoma as discussed by Lagoda et al., Increased Detectability of Somatic Changes in DNA from Human Tumours After Probing with "Synthetic" and "Genome-Derived" Hypervariable Multilocus Probes, *Hum. Genet.* 84:3540 (1989); and breast, adrenal, pancreas and thyroid tumors as discussed by Matsumura, Y. and D. Tarin, DNA Fingerprinting Survey of Various Human Tumors and Their Metastases, *Cancer Res.* 52:2174–2179 (1992). Thus, the present inventors' discovery of an association of specific tumor characteristics with variations in genomic stability of colorectal tumors may be replicated with a similar analysis of interspersed repetitive sequences in other organ tumor systems.

The invention will be further understood with reference to the following illustrative embodiments, which are purely exemplary, and should not be taken as limiting the true scope of the present invention as described in the claims.

EXAMPLE 1

Isolation of Tumor and Normal Tissue DNA and Analysis for Genomic Instability

DNA from 90 colorectal cancers and the corresponding DNA from normal tissue was isolated from 87 patients in the following manner. A hematoxylin and eosin-stained frozen section of each tumor was examined and used as a template to dissect away as much non-tumor tissue as possible in order to enrich for tumor cells. The remaining tumor fragments were remounted for serial frozen sections in Tissue-Tek ornithine carbamyl transferase compound (Miles, Inc., Cat. No. 4583). One hundred 10–20 micron-thick cryostat sections were then made. The first, fiftieth, and one-hundredth sections were stained with hematoxylin and eosin, and the fraction of tumor nuclei present at these levels was assessed by a pathologist. Only those tumors containing $\geq 70\%$ tumor nuclei in each of these three sections were used for subsequent steps. DNA was extracted from tumor and normal control tissue (either normal mucosa or peripheral blood leukocyte) using an Applied Biosystem 340A Nucleic Acid Extractor (ABI, Inc.) in accordance with the manufacturer's instructions and stored at 4° C. until used.

Once the genomic DNA was isolated from the tumors and tissues and prepared as described above, standard polymerase chain reactions were carried out following the methods of J. L. Weber and P. E. May, Abundant Class of Human DNA Polymorphisms Which Can Be Typed Using the Polymerase Chain Reaction, *Am. J. Hum. Genet.* 44:388–396 (1989). The isolated genomic DNA was tested with four primer pairs that hybridize to the flanking DNA of interspersed repetitive sequence loci in the genome. The loci included $(CA)_n$-repeats on chromosome 5 (Mfd 27), chromosome 17 (Mfd 41), chromosome 18 (Mfd 26), and chromosome 15 (635). The primer pairs are set forth in Table 1 and in the Sequence Listing.

All polymerase chain reactions were performed in a Perkin-Elmer Cetus Thermal Cycler. Reaction were carried out in a 25 µl reaction volume comprising:

| | |
|---|---|
| 5.0 µl | 5X Reaction Buffer Containing dNTPs |
| 1.0 µl | First Primer (20 µM) |
| 1.0 µl | Second Primer (20 µM) |
| 1.0 µl | Genomic DNA (250 µg/ml) |
| 0.25 µl | Taq-I polymerase (Perkin Elmer Cetus, 5 units/µl) |
| 0.25 µl | $^{32}$P alpha-dCTP (3000 Ci/mmole) |
| 16.5 µl | sterile $H_2O$ |

The formula for 5X Reaction Buffer Containing dNTPs is as follows:
1 mM dATP
1 mM dCTP
1 mM dGTP
1 mM dTTP
250 mM KCl
50 mM Tris-Cl, pH 8.3
7.5 mM $MgCl_2$
0.05% (w/v) gelatin Samples were kept on ice during mixing and then processed through appropriate temperature cycles for amplification. A typical amplification procedure comprised 30 temperature cycles each consisting of 1 minute at 94° C. (denaturation) and 2 minutes at 55° C. (annealing). Generally, the elongation step of the last cycle was lengthened an additional 10 minutes. Routine variations of these parameters were employed as necessary to optimize the amplification reactions with individual primer pairs. Following this temperature cycling, the reaction volume was brought to 250 ul with $H_2O$. Aliquots of the diluted, amplified DNA were mixed with 2 volumes loading buffer (95% formamide, 20 mM EDTA, 0.05% bromophenol blue, 0.05% xylene cyanol FF), heated at 90° C. for 2 minutes to denature the DNA, and electrophoresed on standard denaturing polyacrylamide DNA sequencing gels. Aliquots of the tumor and tissue DNA from the same patient and amplified using the same primer pair were loaded next to one another in the gel. Gels were then dried and processed for autoradiography. Autoradiograph exposure times were about 2 days at room temperature.

Figure 1A:
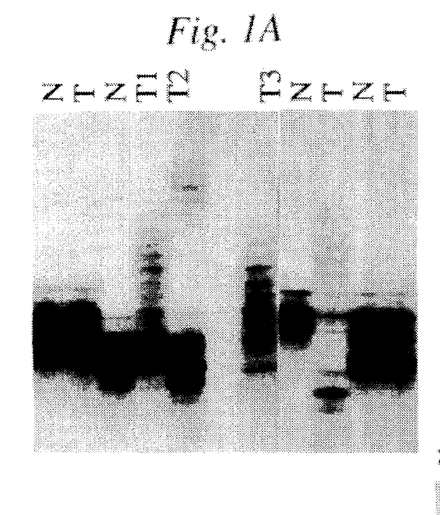
Figure 1B:
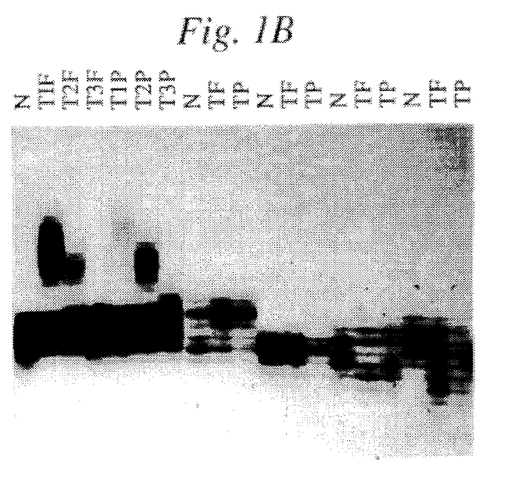

After the autoradiographic film was developed, the lanes containing amplified tumor and tissue DNA were compared to one another to determine the mutational status of the amplified tumor DNA at the locus tested. The film was examined in order to identify whether the banding pattern varied between the tumor and tissue lanes. Generally, multiple bands were detected for each allele: one major band and multiple shadow bands. The shadow bands are thought to be due to PCR artifact (i.e., strand slippage). As shown in FIG. 1, significant variability of fragment sizes reflecting genomic instability was detected in tumor specimens, ranging from a 2 base-pair change in some (Panel B, lane 15 compared to lane 14) to a larger insertion-amplification (panel B, lane 2 compared to lane 1) or deletion in others (Panel A, lane 9 compared to lane 8). Alterations intermediate to these are shown in Panel B, lanes 3 and 18. For purposes of data analysis, two general types of genomic instability were defined. A significant increase (insertion/amplification) or decrease (deletion) in the apparent fragment size compared to the alleles found in DNA from the normal tissue were called Type I mutations (Panel A, lanes 4, 5, 7 and 9; Panel B, lanes 2, 3, 5, 6, 18 and 19). Single two base-pair alterations in the apparent fragment size were called Type II mutations (Panel B, lanes 15 and 16).

Genetic alterations in these microsatellite interspersed repetitive sequence loci were detected in 25 (28%) of the 90 tumors examined. Eight of these 25 positive tumors contained only Type I mutations, 12 contained only Type II mutations, and 5 showed the presence of both Type I and Type II mutations. All 13 tumors that possessed a Type I mutation demonstrated alterations at multiple loci. Of these 13 tumors, nine showed alterations within all $(CA)_n$-repeats examined (Table 2). Tumors having Type II mutations typically showed a change at only a single locus (10 of 17 tumors). Of the 12 tumors with only Type II mutations, ten showed an alteration at only a single $(CA)_n$-repeat (Table 2).

No such genetic alterations were found in any of the paired normal tissues examined.

EXAMPLE 2

Correlations With Loss of Heterozygosity (LOH)

Fourteen probes (see Table 3) detecting DNA polymorphisms on chromosomes 5, 17 and 18 were used to assess the frequency of allelic loss in a group of 91 colorectal cancers. Allelic loss was defined as the demonstration of loss of heterozygosity by one or more of the probes on that chromosome or chromosomal arm.

Tumor and normal tissues were processed and DNA isolated according to the procedures set out in Example 1. The DNA from the tumors and tissues was digested with an appropriate restriction endonuclease, electrophoresed in an 0.8% agarose gel and transferred to a nylon filter from the agarose gel using the method of Southern. Sambrook et al., *Molecular Cloning: A Laboratory Manual*, 2d Ed. (1989), pages 9.31–9.62. The DNA was subsequently hybridized with chromosome-specific $^{32}$P-labelled DNA probe. The gene probes used and their chromosomal positions are shown in Table 3. Hybridization with the labelled probe was detected by autoradiography.

For the 91 tumors analyzed, chromosomes 17 and 18 showed the highest frequency of allelic loss (69% and 70% of tumors, respectively), while a frequency of 48% was noted for chromosome 5 (Table 4). When comparing the relative loss of the two arms of a chromosome, there was no significant difference between loss of 18p versus 18q. For the other two chromosomes analyzed, chromosome arms 5q and 17p showed a higher frequency of loss than the corresponding arms 5p and 17q. It should be noted, however, that 5p and 17q were each analyzed with only one DNA probe.

The presence or absence of Type I and II mutations in the tested microsatellite loci were compared to the presence or absence of allelic loss for chromosomes 5, 17, and 18 as determined by Southern blot analysis. A significant negative correlation was observed between LOH and microsatellite structural changes for each of the three markers evaluated (Table 5). That is, tumors demonstrating genetic instability had infrequent loss of heterozygosity. For example, 14 (22%) tumors did not show LOH for any of the three chromosomes tested. Of these 14 tumors, 12 (80%) exhibited instability at the di-nucleotide repeat loci. These results provide further evidence that a genetic mechanism distinct from disruption of known tumor suppressor genes is operative in tumors displaying Type I and Type II mutations.

EXAMPLE 3

Genomic Instability and Anatomical Site of Tumor

Tumors and corresponding normal tissues were surgically removed from patients and the anatomical site of origin of each tumor was recorded. Tumor and normal tissue DNA was extracted and analyzed for Type I or Type II mutations following the method of Example 1 above. Table 6 demonstrates the association of Type I and Type II mutations with anatomical site of the tumor. Thirteen (87%) of the 15 tumors having multiple mutations (i.e. a tumor demonstrating an alteration at more than one microsatellite locus) arose in the proximal colon. Not all of the proximal tumors demonstrated the presence of this type of alteration. That is, Type I or Type II mutational genomic instability was detected in 13 (34%) of the 38 proximal tumors analyzed. Nevertheless, a clear association of multiple microsatellite structural changes and tumor origin in the proximal colon is demonstrated by these results.

EXAMPLE 4

Clinical Significance of Genomic Instability

The clinical significance of the above-described Type I mutation-related genomic instability was examined. Tumor patients having tumors carrying Type I mutations were compared to patients having colorectal tumors without Type I mutations. All tumors were staged by the Astler-Coller modification of the Dukes' staging system. Astler and Coller, The Prognostic Significance of Direct Extension of Carcinoma of the Colon and Rectum. *Ann. Surg.* 139:846–51 (1954). Statistical analyses were performed with the Statistical Analysis System (SAS®). Overall survival was defined as the time from surgery until the date of death, while tumor recurrence was defined as the time at which recurrence was documented. Both of these endpoints were censored for patients dying of causes other than metastatic colon cancer. Distributions of survival times were compared using the log-rank statistic, Mantel and Haenszel, Statistical Aspects of the Analysis of Data from Retrospective Studies of Disease, *J. Natl. Cancer Inst.* 22:719–48

(1959), and survival distribution curves were estimated by the method of Kaplan and Meier, Nonparametric Estimation from Incomplete Observations, *J. Am. Stat. Assoc.* 58: 457–81 (1958). The reported p-values are two-sided, and statistical significance was defined at a p-value of less than 0.05.

In this analysis, 86 patients having tumors of Dukes stages A-D were analyzed, and no tumor recurrences nor cause-specific deaths were noted in the 12 patients having Type I mutations. In contrast, approximately 30% of patients without Type I mutations experienced tumor recurrence, and approximately 42% of patients without Type I mutations failed to survive. These data provide a statistically significant association of Type I mutation with decreased disease recurrence (p=0.03) and with increased survival (p=0.02). Sixty patients having tumors classified specifically as Dukes stage B or C were analyzed in the same way. This analysis did not yield a statistically significant association due to the smaller sample size (p=0.07 for association with decreased disease: recurrence and p=0.15 for association with increased survival). However, the same pattern was seen as with the Dukes A-D patients: no tumor recurrences nor cause-specific deaths in the 11 patients having Type I mutations, while over 23% of the remaining patients experienced tumor recurrence or failed to survive.

EXAMPLE 5

Analysis of Tri-nucleotide Repeat Locus

DNA was extracted from tumors and normal tissue and standard polymerase chain reactions were carried out using the methods discussed in Example 1 above. A primer pair that binds to the nucleotide sequence flanking a specific repeat of the form $(AGC)_n$ at a defined location within the human TATA-binding protein sequence was selected on the basis of a search of a commercial nucleic acid sequence data base. The DNA sequences of these polymerase chain reaction primers are as follows:

5'-ACTGACCCCACAGCCTATTC-3' (SEQ ID NO: 9)
5'-CAAGGGTGCAGTTGTGAGAG-3' (SEQ ID NO: 10)

These primers are sequences numbered 9 and 10 in the DNA Sequence Listing.

Figure 2:
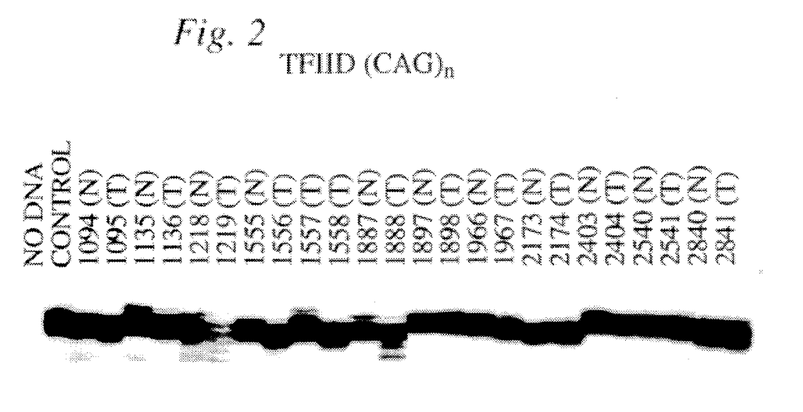
FIG. 2 depicts an autoradiograph of amplified fragments obtained with primer pairs specific for a tri-nucleotide repeat microsatellite locus.

As seen in FIG. 2, some of the tumors exhibited a structural change in the tested trinucleotide repeat locus when compared to the corresponding normal tissues. This can be seen in FIG. 2, for example, by comparing tumor sample number 1556 to its corresponding normal tissue sample number 1555. Some tumors carrying one or more di-nucleotide repeat changes failed to show an alteration within the tested tri-nucleotide repeat locus. Nevertheless, only those samples that demonstrated variation in one or more of the above-described di-nucleotide $((CA)_n)$ repeats also exhibited a structural alteration at the tested tri-nucleotide repeat locus. Such alterations within a trinucleotide repeat region of the human TATA-binding protein could affect protein function.

EXAMPLE 6

DNA Sequence Analysis of Di-Nucleotide Repeats

Figure 3:
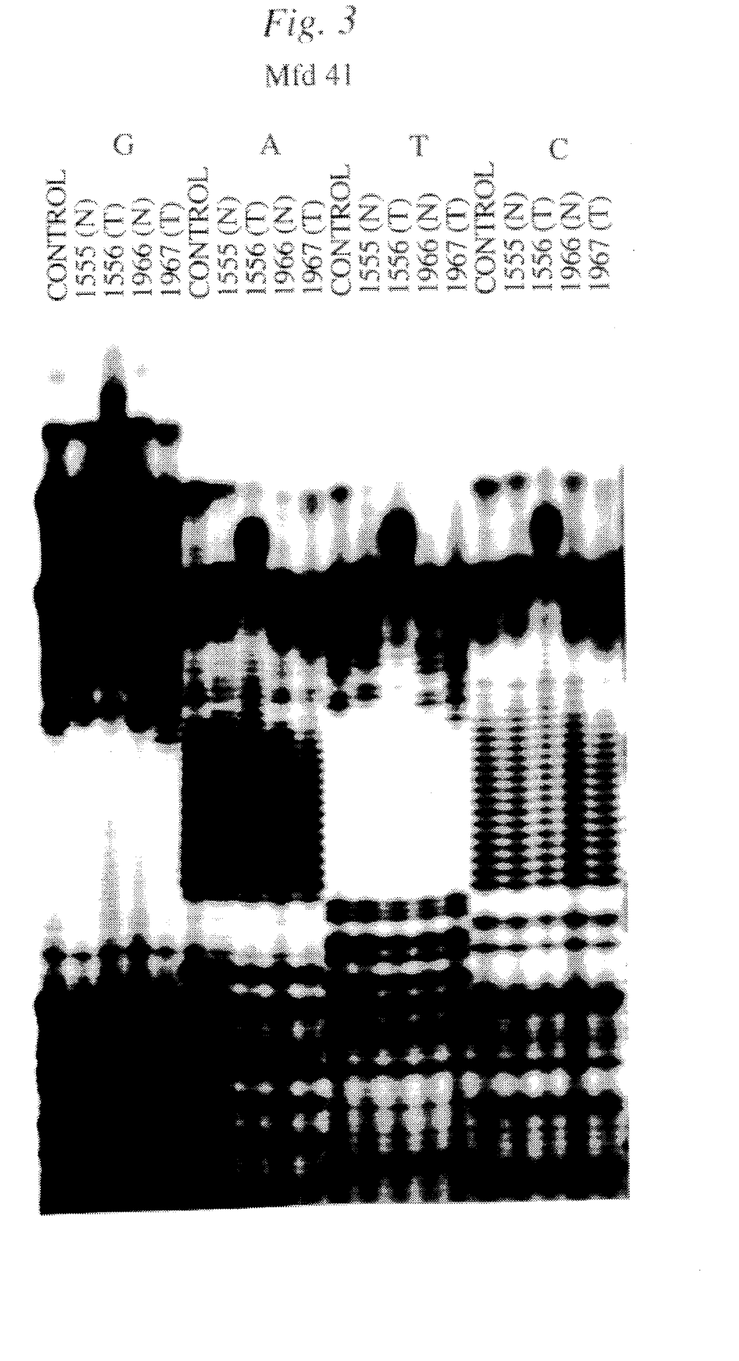
FIG. 3 depicts an autoradiograph of a sequencing gel containing the products of sequencing reactions carried out on amplified fragments obtained with the Mfd 41 primer pair.
Figure 4:
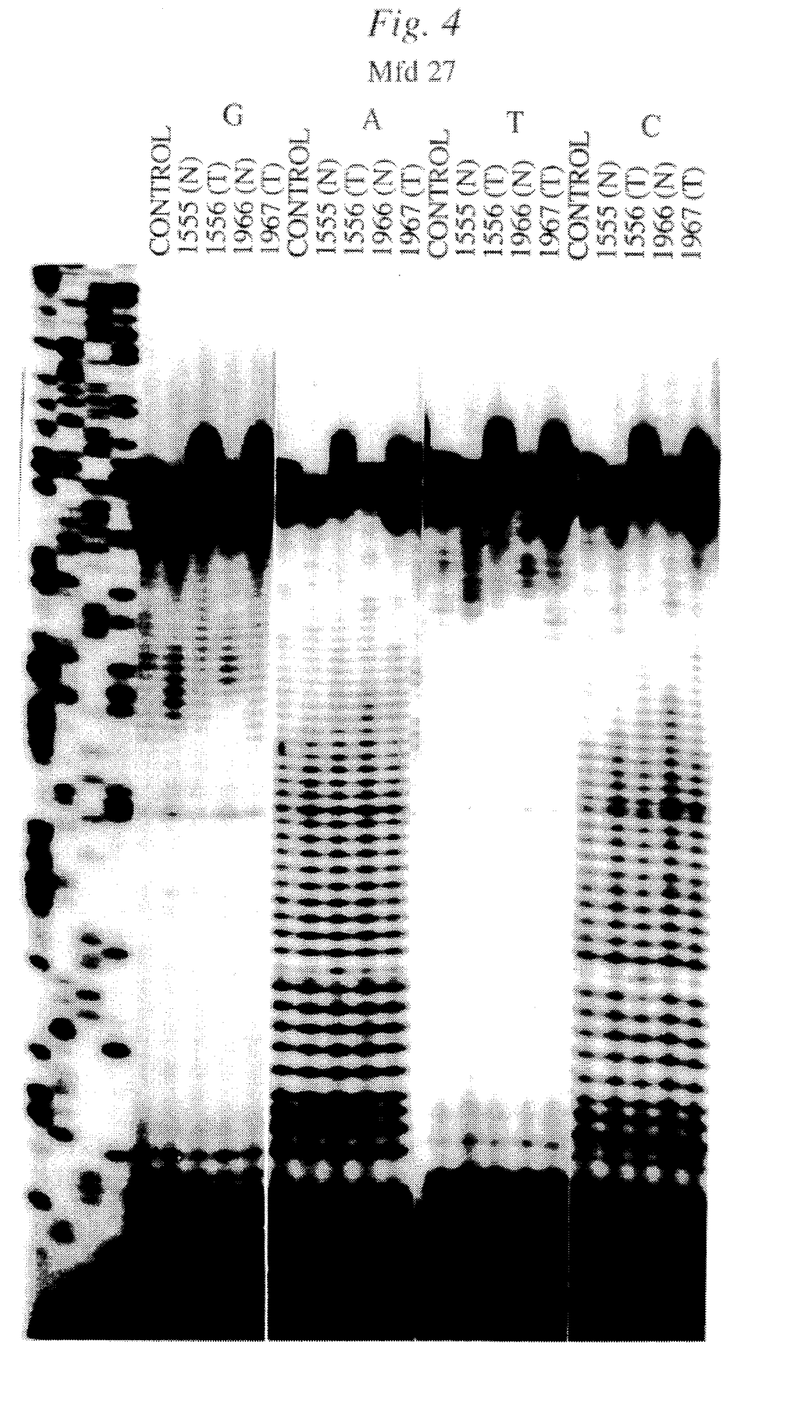
FIG. 4 depicts an autoradiograph of a sequencing gel containing the products of sequencing reactions carried out on amplified fragments obtained with the Mfd 27 primer pair.

DNA sequencing reactions were performed on amplified DNA fragments representing selected di-nucleotide repeat loci in order to confirm the presence of specific structural alterations within each locus. DNA was extracted from tumors and normal tissues. Standard polymerase chain reactions using primer pairs for Mfd 41 and Mfd 27 (Table 1) were carried out using the methods discussed in Example 1 above. The amplified DNA's were sequenced using the Sanger method of dideoxy nucleotide sequencing, with the :same primers as used for the PCR amplifications. The sequencing protocols were essentially those described in the Promega Technical Manual for its fmol™ DNA Sequencing System using Taq DNA polymerase, except that 7-deaza GTP was used in the first PCR reaction. See J. Ellingboe, U. B. Gyllensten, eds., *The PCR Technique: DNA Sequencing* (Eaton Publishing, 1992). The labelled DNA was electrophoresed in denaturing polyacrylamide gels. FIGS. 3 and 4 depict autoradiographs of the sequencing gels.

FIG. 3 depicts products of the sequencing reactions from tumor and corresponding tissue DNA of two patients. Prior to sequencing, the DNAs were amplified using the Mfd 41 primer pair. Samples numbered 1555 and 1556 are DNA from tissue and tumor from one patient and samples numbered 1966 and 1967 are tissue and tumor DNA from another patient. When the lanes containing DNA from sample number 1555 (tissue) are compared to those lanes containing DNA from sample number 1556 (tumor), it is apparent that DNA from sample number 1556 is of a higher molecular weight than DNA from sample number 1555. It is also evident from the autoradiograph of the sequencing gel that the amplified DNA, as expected, contains a region of CA-repeats.

FIG. 4 depicts products of the sequencing reactions from tumor and corresponding tissue DNA of the same two patients as shown in FIG. 3, but with analysis of a different di-nucleotide repeat locus (Mfd 27). The template DNAs were samples numbered 1555, 1556, 1966 and 1967 as discussed above. The sequencing reactions were performed as described above. At this locus, both tumor DNAs varied from the tissue DNAs in the number of di-nucleotide repeats as evidenced by the increased length of the DNA in lanes containing the tumor DNAs. As in FIG. 3, FIG. 4 also shows a CA-rich region.

The foregoing detailed description has been provided for a better understanding of the invention only and no unnecessary limitation should be understood therefrom as some modifications will be apparent to those skilled in the art without deviating from the spirit and scope of the appended claims.

TABLE 1

| | | Primers for Amplification of Di-nucleotide Repeats | | |
|---|---|---|---|---|
| Marker | Locus | Map Position | SEQ. ID NO: | Primer Sequence |
| Mfd 27 | D5S107 | 5q11.2-q13.3 | 1 | GATCCACTTTAACCCAAATAC |
| | | | 2 | GGCATCAACTTGAACAGCAT |
| Mfd 41 | D17S261 | 17p12-p11.1 | 3 | CAGGTTCTGTCATAGGACTA |
| | | | 4 | TTCTGGAAACCTACTCCTGA |

TABLE 1-continued

Primers for Amplification of Di-nucleotide Repeats

| Marker | Locus | Map Position | SEQ. ID NO: | Primer Sequence |
|---|---|---|---|---|
| Mfd 26 | D18S34 | 18q | 5 | CAGAAAATTCTCTCTGGCTA |
|  |  |  | 6 | CTCATGTTCCTGGCAAGAAT |
| 635/636 | cardia muscle actin gene | 15q11-qter | 7 | TTGACCTGAATGCACTGTGA |
|  |  |  | 8 | TTCCATACCTGGGAACGAGT |

Mfd 26, 27, and 41 sequence obtained from James Weber. 635/636 sequence obtained from M. Litt and J. A. Luty, A Hypervariable Microsatellite Revealed by in vitro Amplification of a Dinuclotide Repeat Within the Cardiac Muscle Actin Gene, Am. J. Human Genet. 44:397 (1989).

TABLE 2

Tumors Demonstrating Genomic Instability

| Type of Alteration | Number of Loci Involved/Tumor | | | |
|---|---|---|---|---|
|  | 1 | 2 | 3 | 4 |
| I alone | 0 | 1 | 3 (2) | 4 (3) |
| II alone | 10 | 2 | 0 | 0 |
| I and II | 0 | 0 | 0 | 5 (4) |

( ) = Synchronous tumors omitted

TABLE 3

Chromosomal Location of DNA Probes Utilized

| Probe | Locus Symobol | Location | Restriction Enzyme | Reference |
|---|---|---|---|---|
| pJO71H-A | D5S20 | 5p13 | EcoRI | 1 |
| p105-153A | D5S39 | 5q11.2-q13.3 | MspI | 1 |
| π227 | D5S37 | 5q21 | PstI | 1 |
| C11p11 | D5S71 | 5q14-q21 | TaqI | 1 |
| M4 | D5S6 | 5q11.2-q13.3 | BamHI | 1 |
| J0205H-C | D5S22 | 5q34-qter | MspI | 1 |
| pYNZ22 | D17S30 | 17p13.3 | BamHI | 2 |
| pYNH37.3 | D17S28 | 17p13.3 | TaqI | 1 |
| pTHH 59 | D17S4 | 17q23-q25.3 | TaqI | 1 |
| L2.7 | D18S6 | 18p11 | PstI | 1 |
| pHH64 | TTR | 18q11.2-q12.1 | MspI | 1 |
| DCC 1.9 | DCC | 18q21.3 | EcoRI | 4 |
| p15-65 | D18S8 | 18q21.3 | MspI | 3 |
| pERT25 | D18S11 | 18q23 | PstI | 1 |

1. Cytogenetics and Cell Genetics 58: 1–2200 (1991).
2. Nakamura Y: Nuc Acids Res 16:4707 (1987).
3. Marthans F, et al. Nuc Acids Res 15:1348 (1987).
4. Vogelstein, unpublished results.

TABLE 4

Frequencey of Allelcic Loss on Chromosomes 5, 17 and 18

| Chromosome | Loss No. | %* | No Loss (No.) | NI (No.) |
|---|---|---|---|---|
| 5p | 9 | 20 | 36 | 46 |
| 5q | 40 | 46 | 47 | 4 |
| 5 | 42 | 48 | 46 | 3 |
| 17p | 59 | 69 | 26 | 6 |
| 17q | 29 | 45 | 36 | 26 |
| 17 | 61 | 69 | 28 | 2 |
| 18p | 24 | 69 | 11 | 56 |
| 18q | 59 | 69 | 27 | 5 |
| 18 | 62 | 70 | 27 | 2 |

NI = non-informative
*percentage refers to the number of tumors demonstrating loss of heterozygosity divided by the total number of tumors that were informative for the DNA probes utilized.

TABLE 5

Association of DNA Alterations with Loss of Heterozygosity

| | | NL | L | |
|---|---|---|---|---|
| | | | 5q | |
| MFD 27 | Neg | 34 (33) | 37 (36) | |
| | I | 11 (8) | 1 | p < 0.025 |
| | II | 1 | 2 | |
| | | | 17p | |
| MFD 41 | Neg | 17 (16) | 56 (55) | |
| | I | 7 (6) | 1 (0) | p < 0.0005 |
| | II | 2 | 0 | |
| | | | 18q | |
| MFD 26 | Neg | 15 (14) | 52 (51) | |
| | I | 10 (8) | 0 | p < 0.0005 |
| | II | 1 | 4 | |

NL = no loss
L = loss
( ) synchronous tumors omitted

TABLE 6

Association of DNA Alterations with Anatomical Site

| | | C | AC | HF | TC | SF | DC | S | R | P | D | |
|---|---|---|---|---|---|---|---|---|---|---|---|---|
| MFD27 | Neg | 15 | 4 | 2 | 5 | 1 | 2 | 20 (19) | 26 (25) | 26 | 49 (47) | p = 0.003 |
| | I | 5 (4) | 4 (3) | 1 | 1 (0) | 0 | 0 | 0 | 1 | 11 (8) | 1 | |
| | II | 0 | 1 | 0 | 0 | 0 | 0 | 0 | 2 | 1 | 2 | |
| 635 | Neg | 15 | 3 | 2 | 5 | 1 | 2 | 19 (18) | 23 (22) | 25 | 45 (43) | p = 0.018 |
| | I | 3 (2) | 4 | 0 | 1 (0) | 0 | 0 | 0 | 1 | 8 (6) | 1 | |
| | II | 2 | 2 (1) | 1 | 0 | 0 | 0 | 1 | 5 | 5 (4) | 6 | |
| MFD41 | Neg | 16 | 4 | 2 | 6 (5) | 1 | 2 | 20 (19) | 28 | 28 (27) | 51 (50) | p = 0.003 |
| | I | 3 (2) | 5 (4) | 0 | 0 | 0 | 0 | 0 | 0 | 8 (6) | 0 | |
| | II | 1 | 0 | 1 | 0 | 0 | 0 | 0 | 0 | 2 | 0 | |
| MFD26 | Neg | 15 | 4 | 1 | 5 | 1 | 2 | 18 (17) | 27 (26) | 25 | 48 (46) | |

TABLE 6-continued

Association of DNA Alterations with Anatomical Site

|  | C | AC | HF | TC | SF | DC | S | R | P | D |  |
|---|---|---|---|---|---|---|---|---|---|---|---|
| I | 4 (3) | 4 (3) | 1 | 1 (0) | 0 | 0 | 0 | 1 | 10 (7) | 1 | p = 0.006 |
| II | 1 | 1 | 0 | 0 | 0 | 0 | 2 | 1 | 2 | 3 |  |
| Tumors demonstrating mutations at |  |  |  |  |  |  |  |  |  |  |  |
| ≦1 | 15 | 3 | 1 | 5 | 1 | 2 | 20 (19) | 26 | 24 | 49 (48) | p = 0.003 |
| or ≧2 loci | 5 (4) | 6 (5) | 1 | 1 (0) | 0 | 0 | 0 | 2 | 13 (10) | 2 |  |

C caecum
AC ascending colon
HF hepatic flexure
TC transverse colon
SF splenic flexure
DC descending colon
S sigmoid
R rectum
P proximal colon
D distal colon
( ) with synchronous tumors omitted

---

We claim:

1. A method for classifying a malignant colorectal tumor as having disseminated genomic instability as a prognostic indicator for a patient having said malignant colorectal tumor, comprising:
  (a) providing genomic DNA obtained from a sample of said malignant colorectal tumor, said sample having an operable fraction of tumor cells;
  (b) providing genomic DNA obtained from a tissue sample of said patient, said tissue sample being operably free of tumor cells;
  (c) comparing the size of at least one microsatellite sequence locus in said malignant colorectal tumor sample DNA with the size of the corresponding at least one microsatellite sequence locus in said tissue sample DNA; and
  (d) classifying said malignant colorectal tumor as having disseminated genomic instability if the size of said at least one microsatellite sequence locus in said malignant colorectal tumor sample DNA differs from the size of the corresponding at least one microsatellite sequence locus in said tissue sample DNA.

2. A method for evaluating the clinical prognosis of a patient having a malignant colorectal tumor, comprising:
  (a) providing genomic DNA obtained from a sample of said malignant colorectal tumor, said sample having an operable fraction of tumor cells;
  (b) providing genomic DNA obtained from a tissue sample of said patient, said tissue sample being operably free of tumor cells;
  (c) comparing the size of at least one microsatellite sequence locus in said malignant colorectal tumor sample DNA with the size of the corresponding at least one microsatellite sequence locus in said tissue sample DNA; and (d) correlating said comparative size of said at least one microsatellite sequence locus in said malignant colorectal tumor sample DNA with the clinical prognosis of said patient.

3. The method of claim 1 wherein said microsatellite sequence is a dinucleotide repeat sequence.

4. The method of claim 1 wherein said microsatellite sequence is a trinucleotide repeat sequence.

5. The method of claim 3 wherein said di-nucleotide repeat sequence is of the form $(CA)_n \cdot (GT)_n$.

6. The method of claim 1 wherein said comparison of at least one microsatellite sequence locus comprises selecting appropriate primers for polymerase-based amplification of said at least one locus, amplifying said at least one locus in said malignant colorectal tumor sample DNA and in said tissue sample DNA, and comparing the apparent fragment sizes of said amplified DNA's.

7. The method of claim 6 wherein said at least one locus comprises at least two unlinked loci.

8. The method of claim 6 wherein said polymerase-based amplification is by polymerase chain reaction.

9. The method of claim 2 wherein said microsatellite sequence is a dinucleotide repeat sequence.

10. The method of claim 2 wherein said microsatellite sequence is a trinucleotide repeat sequence.

11. The method of claim 9 wherein said di-nucleotide repeat sequence is of the form $(CA)_n \cdot (GT)_n$.

12. The method of claim 2 wherein said comparison of at least one microsatellite sequence locus comprises selecting appropriate primers for polymerase-based amplification of said at least one locus, amplifying said at least one locus in said malignant colorectal tumor sample DNA and in said tissue sample DNA, and comparing the apparent fragment sizes of said amplified DNA's.

13. The method of claim 12 wherein said at least one locus comprises at least two unlinked loci.

14. The method of claim 12 wherein said polymerase-based amplification is by polymerase chain reaction.

* * * * *

Adverse Decisions In Interference

Patent No. 5,578,450, Steven N. Thibodeau, METHOD FOR CLASSIFYING A TUMOR, Interference No. 103,859, final judgment adverse to the patentee rendered May 15, 2000, as to claims 1-14.
*(Official Gazette October 17, 2000)*